(12) United States Patent
Schwieger

(10) Patent No.: US 8,174,371 B2
(45) Date of Patent: May 8, 2012

(54) PORTABLE VIBRATING DEVICE AND METHOD OF USE

(76) Inventor: Jeffrey L. Schwieger, Shakopee, MN (US)

( * ) Notice: Subject to any disclaimer, the term of this patent is extended or adjusted under 35 U.S.C. 154(b) by 402 days.

(21) Appl. No.: 12/439,255

(22) PCT Filed: Aug. 30, 2007

(86) PCT No.: PCT/US2007/077194
§ 371 (c)(1),
(2), (4) Date: Feb. 27, 2009

(87) PCT Pub. No.: WO2008/028016
PCT Pub. Date: Mar. 6, 2008

(65) Prior Publication Data
US 2010/0013610 A1    Jan. 21, 2010

Related U.S. Application Data

(60) Provisional application No. 60/824,346, filed on Sep. 1, 2006.

(51) Int. Cl.
*H04B 3/36*    (2006.01)
(52) U.S. Cl. .......................... 340/407.1; 340/7.6; 600/38
(58) Field of Classification Search ............. 340/407.1, 340/311.2, 691, 683, 4.12, 7.6, 286.11; 310/323.02, 310/81, 12.14, 311; 257/E21.481, E21.518; 318/114; 601/69, 70, 38, 46, 72, 84; 128/898; 600/38
See application file for complete search history.

(56) References Cited

U.S. PATENT DOCUMENTS

| | | | |
|---|---|---|---|
| 3,277,358 A | 10/1966 | Nicholl | |
| 4,979,502 A | 12/1990 | Hunt | |
| 5,436,548 A | 7/1995 | Thomas | |
| 5,488,351 A * | 1/1996 | Hedayatnia et al. | 340/407.1 |
| 5,613,259 A | 3/1997 | Craft | |
| 5,637,065 A * | 6/1997 | Chang | 482/114 |
| 6,200,193 B1 * | 3/2001 | Nadel | 446/409 |
| 6,411,050 B1 | 6/2002 | Yoshinari | |
| 6,419,649 B1 | 7/2002 | Klein | |
| 6,845,537 B2 * | 1/2005 | Wong | 15/22.1 |
| 7,148,583 B1 * | 12/2006 | Shau et al. | 290/1 R |
| 7,236,087 B2 * | 6/2007 | Vasquez et al. | 340/311.2 |
| 7,554,224 B2 * | 6/2009 | Roberts | 310/15 |
| 2004/0227617 A1 | 11/2004 | Vasquez | |
| 2004/0251750 A1 | 12/2004 | Cheung | |

OTHER PUBLICATIONS

International Search Report and Written Opinion, dated Apr. 11, 2008 for PCT Application No. PCT/US2007/077194, 6 pages.

* cited by examiner

*Primary Examiner* — Toan N Pham
(74) *Attorney, Agent, or Firm* — Fredrikson & Byron, PA

(57) ABSTRACT

A vibrating device that operates without the need for replacement batteries is disclosed. An apparatus is disclosed for generating electrical power and supplying electrical power to a portable vibrating device. A portable vibrating device in accordance with certain embodiments of the invention is adapted to generate and store its own electrical energy, and is adapted to vibrate to alert a user of the device, or to provide various forms of stimulation to a user of the device.

22 Claims, 4 Drawing Sheets

PORTABLE VIBRATING DEVICE AND METHOD OF USE

CROSS-REFERENCE TO RELATED APPLICATIONS

The present application claims priority to International Application No. PCT/US2007/077194 filed 30 Aug. 2007, which in turn claims priority to U.S. Provisional Application No. 60/824,346 filed 1 Sep. 2006, the teachings of all of which are incorporated herein by reference.

FIELD

The invention relates generally to an apparatus for supplying electrical power to a vibrating device, and more particularly to a portable vibrating device which vibrates to alert, or provide stimulation to, a user of the device.

BACKGROUND

A number of devices exist which vibrate to provide a signal to a user. Examples include paging devices (e.g., pagers) and cell phones operated in a vibrate mode. Vibrating devices also exist for providing therapy to a user of the device (e.g., personal massage units, sexual aids, toothbrushes). Such devices are typically portable, and may be handheld or wearable devices. Such devices are often powered by replaceable batteries, or may alternately receive power via a power cord plugged into a standard AC wall outlet.

Power cords tend to be cumbersome, however, and may limit the range of use or portability of a device. Batteries provide enhanced portability to certain devices, although batteries wear out with use and need to be replaced periodically. Replacement of batteries requires opening a battery compartment, removing the worn batteries, and replacing them with new batteries which must be purchased separately. Battery replacement creates waste, puts additional wear and tear on the device, and may even create problems with certain devices (e.g., exposure of fluids to the battery compartment). What is needed therefore are portable vibrating devices that operate without the need for replacement batteries.

BRIEF DESCRIPTION OF THE DRAWINGS

The present invention will hereinafter be described in conjunction with the following drawing figures, wherein like numerals denote like elements.

DETAILED DESCRIPTION

Figure 1:
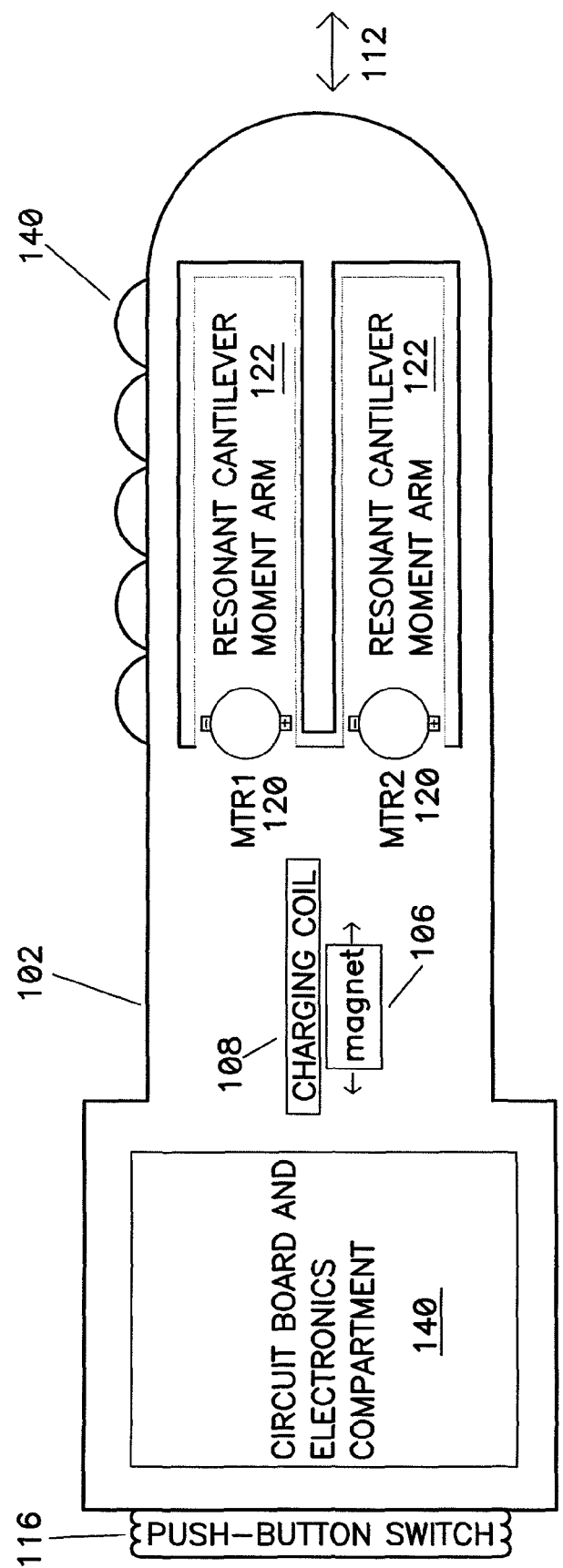
FIG. 1 is a schematic diagram of a portable vibrating device in accordance with an embodiment of the invention.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention as claimed.

Embodiments of the invention include generally portable personal devices for producing vibrational energy and for delivering and/or indicating the vibrational energy to a user of the device without the need for replacement batteries. Certain embodiments generate and store electrical energy utilizing an electromagnetic charging circuit to convert mechanical energy to electrical energy. In some embodiments, mechanical energy is imparted to a device by a user to cause relative motion between a magnet and a charging coil, thereby inducing a voltage in the charging coil. The induced voltage may cause electrical energy to be stored in the device, and the stored energy may be used to power a vibrational motor upon activation of a switch, for example, according to certain embodiments of the invention.

FIG. 1 is a schematic diagram of a vibrating device in accordance with an embodiment of the invention. FIG. 1 illustrates one possible embodiment of the invention, showing exemplary locations of various elements. For example, housing 102 may contain a magnet 106, and a charging coil 108, such that movement of the magnet 106 relative to the coil 108 (e.g., generally along the directions indicated by arrow 112) causes a voltage to be induced in coil 108. Movement of the magnet 106 relative to the coil 108 may be caused by movement of the housing 102 generally with respect to an axis of the housing, such as a longitudinal axis, or along the directions generally indicated by arrow 1 12.

In certain embodiments of the invention, the magnet 106 may move relative to the housing 102 and coil 108, with the coil remaining in a relatively fixed position within the housing 102. Alternately, the coil 108 may be caused to move relative to the magnet 106, with the magnet 106 remaining in a relatively fixed position within the housing 102. In some embodiments, both the magnet 106 and coil 108 may move relative to the housing 102, provided that they move relative to each other during movement of the housing 102.

With continued reference to FIG. 1, vibration motor 120 is also shown disposed within housing 102. Electrical energy generated by relative motion between magnet 106 and charging coil 108 may be stored by a charging circuit and/or storage device, which may be incorporated on a circuit board and disposed in an electronics compartment 140 within housing 102, for example, or may be located elsewhere in housing 102. A circuit board within housing 102 may contain one or more capacitors for storing a generated voltage, and may alternately (or additionally) include one or more rechargeable batteries. Placement of various electrical or electronic components within a housing that does not need to be opened (e.g., in order to replace batteries), for example, may allow the housing to provide a watertight enclosure for such components (e.g., a watertight enclosure for the electrical energy generating source), according to certain embodiments of the invention.

Certain embodiments of the invention may include massage surface 140, as shown in FIG. 1. Massage surface 140 may comprise rollers, or ball bearings, or ribbed, flexible surfaces. Massage surface 140 may be used to deliver a therapeutic massage to a user when caused to vibrate by vibration motor 120. In some embodiments, massage surface 140 may be adapted to deliver a sexually stimulating sensation to a user. For example, housing 102 may be shaped and sized appropriately to simulate sexual activity, and massage surface 140 may include a textured, flexible surface (e.g., formed of a textured silicone rubber or similar material) to provide a sexually pleasing contact surface.

In operation, magnet 106 is caused to move relative to charging coil 108 to generate electrical energy. In certain embodiments, relative motion between magnet 106 and charging coil 108 may be caused by moving housing 102. Either the magnet 106 or the charging coil 108 may be affixed to housing 102, such that motion of housing 102 causes the other component (i.e., either the charging coil 108 or the magnet 106) to move to cause relative motion between the two components. In some embodiments, the shape of housing 102, as well as the shape and orientation of magnet 106 and charging coil 108 within housing 102, may suggest a direction of motion 112 for moving housing 102 to generate electrical energy. As shown in FIG. 1, direction of motion 112 may be generally aligned with a longitudinal axis of housing 102, according to certain embodiments. This may, for example, allow for greater relative motion between magnet 106 and charging coil 108, by providing a longer path of travel therebetween.

Moving the housing 102 to generate electrical energy may be performed by a user of some embodiments by moving the housing 102 in a reciprocating (back-and-forth) motion (e.g., shaking the housing), preferably generally along direction of motion 112, to cause relative motion between magnet 106 and charging coil 108. Some embodiments of the invention may allow a reciprocating motion to be imparted to the housing via external forces, such as via wind or vibration energy from its surroundings. Examples of suitable electrical energy generating mechanisms which rely on relative motion between a magnet and coil are provided in U.S. Patent Application Publication No. 2004/0251750, the contents of which are hereby incorporated by reference in relevant part.

FIG. 1 also shows an embodiment of the invention including a switch (e.g., push-button switch 116), which may be operated by a user to turn the vibration motor 120 either on or off as desired. Switch 116 is shown disposed on an exterior surface and at one end of housing 102, but may be located anywhere on or near the housing 102, according to the intended use of a particular embodiment.

Figure 2:
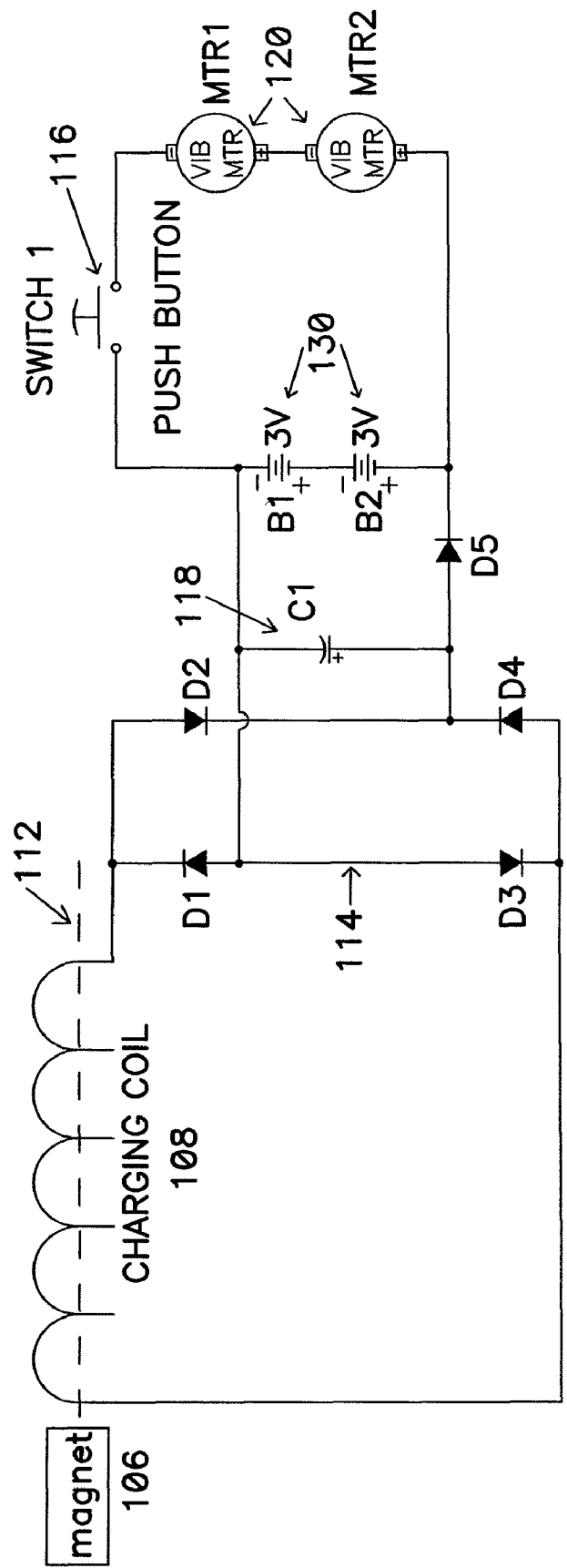
FIG. 2 is an exemplary circuit diagram of a portable vibrating device in accordance with an embodiment of the invention.

FIG. 2 shows an exemplary circuit diagram for a device in accordance with certain embodiments of the invention. Magnet 106 is shown in FIG. 2 aligned to move in a reciprocating manner (e.g., a back-and-forth manner), generally along direction of motion 112 relative to charging coil 108. Alternately, certain embodiments may allow charging coil 108 to move relative to magnet 106 generally along direction of motion 112. Magnet 106 may be elongate, and may be adapted to move longitudinally within (e.g., through a central portion or lumen of) charging coil 108 according to an embodiment of the invention. Alternate configurations could be devised by one of ordinary skill in the art without departing from the scope of the claimed invention.

An exemplary charging circuit 114 is also shown in FIG. 2. In the particular example shown, charging circuit 114 includes a rectifier (e.g., a bridge rectifier) formed from four diodes, D1-D4, and a capacitor C1 for charging and storing electrical energy (e.g., a voltage across capacitor C1). In the example shown in FIG. 2, diodes D1-D4 are arranged to form a full-wave bridge rectifier that will allow electrical energy to flow in only one direction through capacitor C1. In operation, as magnet 106 passes through the windings of charging coil 108, a voltage is induced in the coil. The polarity of the induced voltage is determined by the direction of travel of the magnet 106 through coil 108. Thus, a reciprocating motion of magnet 106 with respect to charging coil 108 will cause the induced voltage across coil 108 to oscillate in polarity. The rectifier of charging circuit 114 causes the voltage stored across capacitor C1 to be of a single polarity. Capacitor C1 may thereby serve as an electrical energy storage device to store electrical energy for powering vibration motor 120 when desired by a user.

Capacitor C1 may have a capacitance value chosen to provide the energy storage requirements for the intended device uses. For certain embodiments, a capacitance rating of 0.22 Farads (e.g., at 5 volts), for example, may be suitable for supplying the electrical energy requirements of vibration motors that may be used in certain portable or handheld devices. Of course, other alternate configurations of charging circuits may be employed by one of ordinary skill in the art, and would be deemed to fall within the scope of the claimed invention. For example, silicon controlled rectifier (SCR) circuitry, other types of bridge rectifier circuits, and Zener diode circuits may be arranged to form the rectifier of charging circuitry 114, as would be apparent to one of ordinary skill in the art.

In some embodiments, such as the one illustrated in FIG. 2, charging circuit 114 may include one or more rechargeable batteries (e.g., B1 and B2 in FIG. 2) to serve as an electrical energy storage device. Rechargeable batteries B1, B2, may be used instead of capacitor C1, or may be used in conjunction with capacitor C1 to serve as the electrical energy storage device, as shown in FIG. 2. In the particular embodiment shown, rechargeable batteries B1, B2 are 3 volt rechargeable batteries (e.g., lithium or lithium ion batteries), although other types of rechargeable batteries and other voltage ratings may be found to be suitable by one of ordinary skill in the art. Voltage regulator circuitry (not shown in FIG. 2) may also be used in conjunction with capacitor C1 and/or batteries B1, B2, in order to maintain a proper operating voltage for vibration motor 120, as would be known by one of ordinary skill in the art.

Charging circuit 114, as well as any voltage regulator circuitry, may be incorporated on a circuit board and disposed in an electronics compartment 140 (as shown and described above with respect to FIG. 1) within housing 102, for example, or may be located elsewhere in housing 102. The circuit board may contain one or more capacitors for storing a generated voltage, and may alternately (or additionally) include one or more rechargeable batteries, generally as described above.

The one or more vibrating motors 120 are adapted to impart vibrational energy to the housing 102, which may then be sensed (e.g., felt, heard, or seen) by a user of the device. In certain embodiments, the amount of vibration energy delivered from the housing 102 to a user, for example, may be magnified by coupling the vibration motor 120 to a cantilever moment arm 122 (see FIG. 1). In the embodiment illustrated in FIG. 1, for example, a large gain (up to three-fold or more) in mechanical vibration force may be realized at the end of the cantilever moment arm by operating the vibrating motor 120 at a resonant frequency of the moment arm 122, as would be appreciated by one of ordinary skill in the art with the benefit of these teachings.

Figure 3A:
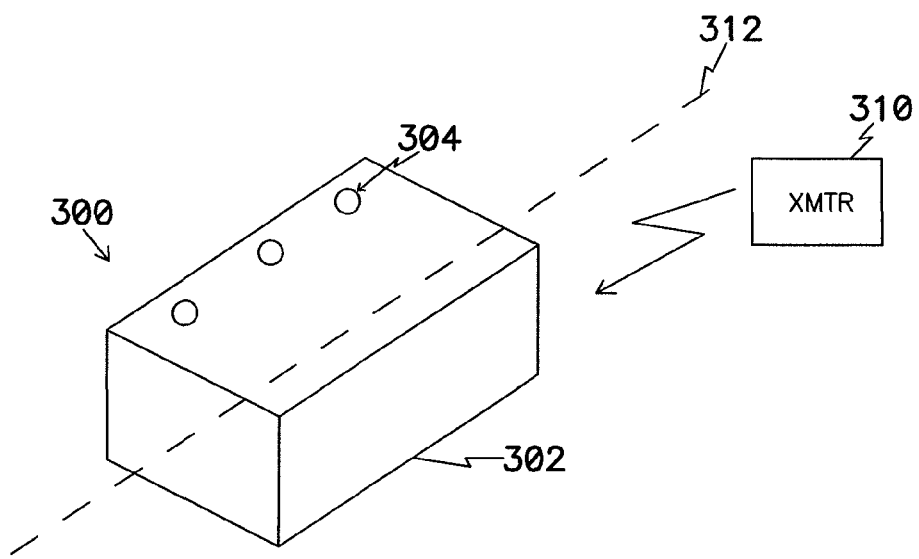
FIG. 3(a) is a schematic perspective view of a paging system in accordance with an embodiment of the invention.
Figure 3B:
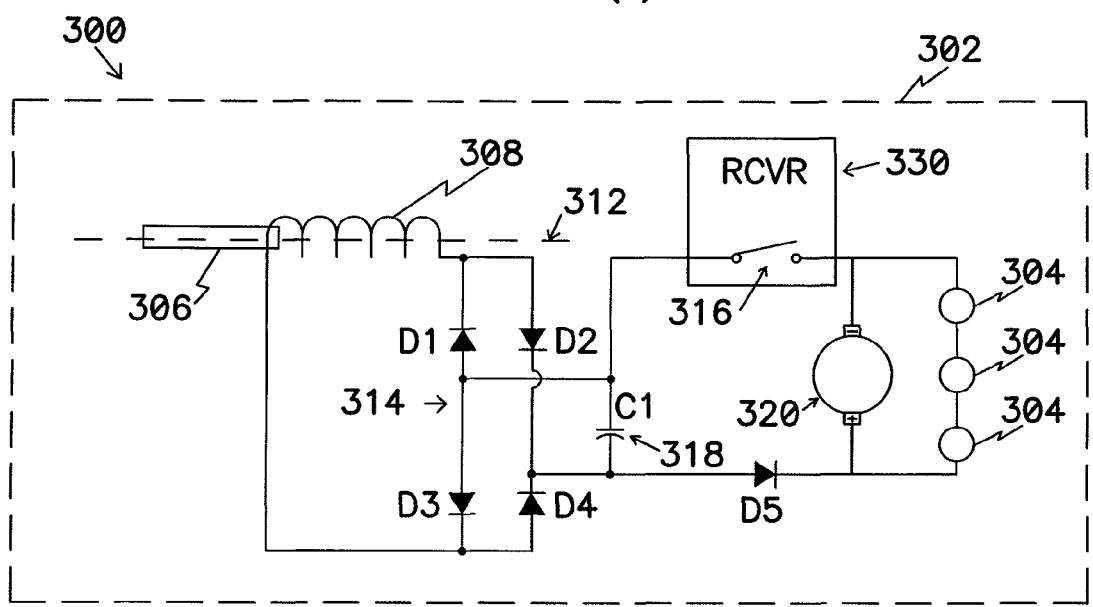
FIG. 3(b) is an exemplary circuit diagram of a vibrating paging device in accordance with an embodiment of the invention.

FIG. 3(a) is a schematic perspective view of a paging system in accordance with an embodiment of the invention. FIG. 3(b) is an exemplary circuit diagram of a portable paging device 300 that may be used as part of the system illustrated in FIG. 3(a), in accordance with an embodiment of the invention. A paging device 300 may be comprised of a housing 302 which is adapted to deliver vibration energy to its surroundings when an appropriate paging signal is received from a transmitting station 310. Paging devices 300 may include pagers, which can provide visual indications 304 in addition to vibration energy upon receipt of a paging signal. Visual indication 304 may include flashing lights, such as that illustrated in FIG. 3(a), or may include LED readouts or other forms of visual indications to supplement the vibration energy.

Other examples of paging devices 300 include restaurant pagers, used in conjunction with patron paging systems, for example to notify a waiting patron that a table is ready and available for them to use.

Although embodiments of the invention are clearly not so limited, certain embodiments may find utility in applications in which the intended use is temporary in nature. For example, the use of the restaurant pager embodiment just described might typically involve a restaurant host moving (e.g., shaking) the device in a reciprocating manner, then handing the device to a restaurant patron who would typically not expect to have to wait much more than about an hour for a table to become available. Of course, the "temporary" use or certain embodiments may extend much longer than an hour, and may extend for 3, or 5, or 10 hours, or possible for more than a day. In some embodiments of the invention, an indicator light (e.g., and LED) may be provided to indicate that the shaking (movement) of the device has caused an amount of electrical energy to be stored that should suffice for the intended purpose of the device. For example, after shaking vigorously for 15 seconds, a colored (e.g., green) LED on the device might illuminate to indicate that a certain restaurant pager embodiment should function properly for a 3-hour period, or it might indicate that a personal massage/stimulation device should function properly for a 45-minute period. Of course, other similar variants will become apparent to those of ordinary skill in the art and would be considered to fall within the scope of the invention as claimed below.

In accordance with an embodiment of the invention, paging device 300 may generate electrical energy by causing relative motion between a magnet 306 and a coil 308 disposed within housing 302 of paging device 300. As shown in FIG. 3(b), paging device 300 contains similar elements as shown and described above with respect to FIGS. 1 and 2. In the particular example shown, paging device 300 has a longitudinal axis 312. Relative motion between magnet 306 and coil 308 may be caused by moving housing 302 generally along the longitudinal axis 312 in a reciprocating manner, substantially as described above. Electrical energy is thereby induced in coil 308, and may be charged and stored using charging circuit 314 in a manner similar to that described above with respect to FIGS. 1 and 2.

FIG. 3(b) shows capacitor 318 and vibration motor 320 with receiver 330 disposed therebetween. Receiver 330 is adapted to receive an appropriate paging signal from transmitting station 310 (see FIG. 3(a)), and to cause switch 316 to close in response thereto. In operation, the paging signal causes switch 316 to close, and electrical energy is thereby supplied to vibration motor 320 from capacitor 318. In certain embodiments of the invention, rechargeable batteries may be incorporated, either alone or in conjunction with capacitor 318, as described above with respect to FIG. 2. In some embodiments, lights 304 may also serve as visual indicators of a received paging signal, to supplement the vibration energy sensed by the user. Lights 304 may comprise LEDs according to some embodiments.

Figure 4A:
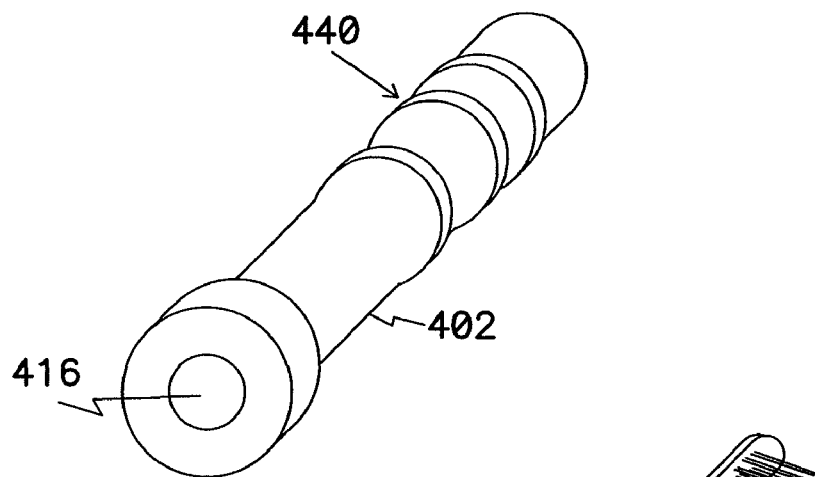
FIG. 4(a) is a perspective view of a personal vibrating massage device in accordance with an embodiment of the invention.

FIG. 4(a) is a perspective view of a personal vibrating massage device in accordance with an embodiment of the invention. The device of FIG. 4(a) comprises a housing 402, and includes a pushbutton switch 416 to allow a user to manually turn on vibration energy for applying massage therapy. In certain embodiments, the vibrating massage device may include a massage surface 440, which may comprise rollers, or ball bearings, or ribbed, flexible surfaces. Massage surface 440 may be used to deliver a therapeutic massage to a user when caused to vibrate by vibration motor 420 (see FIG. 4(c)). In some particular embodiments, massage surface 440 may be adapted to deliver a sexually stimulating sensation to a user. For example, housing 402 may be shaped and sized appropriately to allow for the simulation of sexual activity, and massage surface 440 may include a textured, flexible surface (e.g., formed of a textured silicone rubber or similar material) to provide a stimulating or pleasing contact surface for a user (e.g., for direct contact with a user's skin, including erogenous zones).

In some embodiments, the personal massage device of FIG. 4(a) may optionally include the ability to provide heat energy to a user, for example, at or near massage surface 440, or at other portions of housing 402 (e.g., areas intended to come into contact with the portion of a user's body in which heat therapy is desired). Heat therapy may be provided in such a device, either alone, or in conjunction with vibration therapy, according to various embodiments of the invention.

Figure 4B:
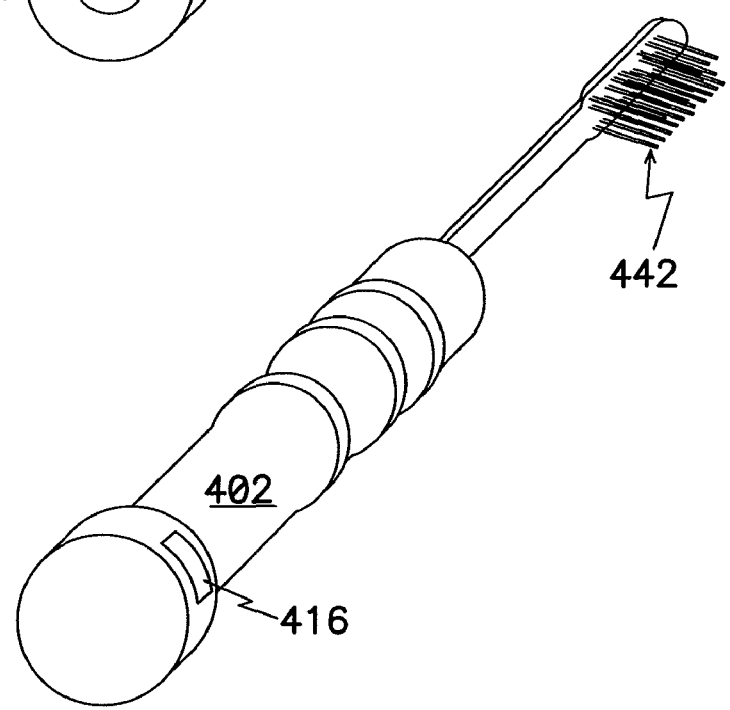
FIG. 4(b) is a perspective view of an electric toothbrush in accordance with an embodiment of the invention.
Figure 4C:
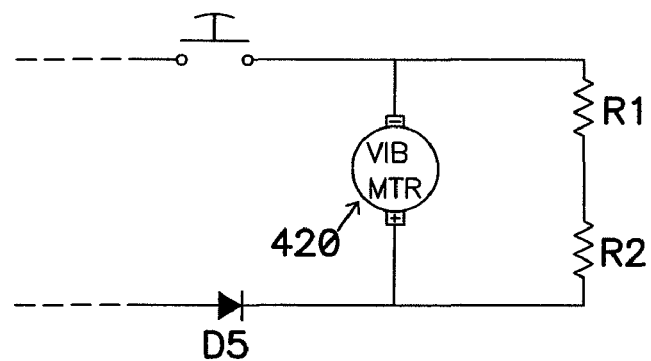
FIG. 4(c) is a partial schematic circuit diagram for an alternate embodiment of the personal vibrating massage device of FIG. 4(a).

FIG. 4(c) is a partial schematic circuit diagram for an embodiment of the personal vibrating massage device of FIG. 4(a) which includes both a vibration motor 420 and heating elements R1 and R2. Heating elements may be formed of resistive components which generate heat according to the equation, $P=I^2*R$, where I is the electrical current flowing through resistive elements R1 and R2, and R is the respective resistance value. Resistance values may be chosen in conjunction with a desired voltage level (e.g., the operating voltage for the vibration motor 420), such that a suitable amount of heat energy is generated and delivered to a user during operation of the massage device.

FIG. 4(b) is a perspective view of an electric brush in accordance with an embodiment of the invention. The electric brush of FIG. 4(b) is similar in construction to the embodiments described thus far, including a manual switch 416 and a housing 402 for enclosing electrical energy generation mechanisms and charging circuitry. The electric brush may include bristles 412 for imparting vibrational energy to a user's teeth or hair, for example, according to certain particular embodiments of the invention.

Thus, a PORTABLE VIBRATING DEVICE has been described. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A portable sexual stimulation device comprising:
an elongated housing that includes an exterior massaging surface configured to provide a sexually stimulating sensation, the elongated housing defining a longitudinal axis;
an electrical energy generating source operatively coupled to the elongated housing, the electrical energy generating source comprising a magnet and a charging coil, the magnet and charging coil adapted to move relative to one another to thereby generate electrical energy in the coil;
a charging circuit adapted to receive electrical energy generated by the electrical energy generating source, the charging circuit comprising a rectifier and an electrical energy storage device;
a vibration motor coupled to the elongated housing, the vibration motor adapted to receive electrical energy from the electrical energy storage device, the vibration motor further adapted to impart vibrational energy to the elongated housing;
a switch adapted to deliver electrical energy from the electrical energy storage device to the vibration motor when the switch is closed;
wherein movement of the elongated housing generally along the longitudinal axis in a reciprocating manner causes the magnet and coil to move relative to one another.

2. The device of claim 1 wherein the portable device is a handheld or wearable device that does not require replacement batteries.

3. The device of claim 1 wherein the electrical energy generating source is housed entirely within the elongated housing, and wherein the elongated housing provides a watertight enclosure for the electrical energy generating source.

4. The device of claim 1 wherein the vibration motor is coupled to the elongated housing via a cantilever moment arm.

5. The device of claim 4 wherein the vibration motor is adapted to operate at a resonant frequency of the cantilever moment arm to accentuate the vibrational energy imparted to the elongated housing.

6. The device of claim 1 wherein the magnet is adapted to be movable with respect to the elongated housing.

7. The device of claim 1 wherein the charging coil is adapted to be movable with respect to the elongated housing.

8. The device of claim 1 wherein the rectifier is a full wave bridge rectifier.

9. The device of claim 1 wherein the electrical energy storage device comprises one or more capacitors.

10. The device of claim 1 wherein the electrical energy storage device comprises one or more rechargeable batteries.

11. The device of claim 10 wherein the electrical energy storage device comprises two or more rechargeable batteries connected in series.

12. The device of claim 10 wherein the rechargeable batteries are Lithium batteries.

13. The device of claim 10 wherein the rechargeable batteries are Lithium ion batteries.

14. The device of claim 1 wherein the electrical energy storage device comprises at least one rechargeable battery connected in parallel with at least one capacitor.

15. The device of claim 1 further comprising one or more heating elements adapted to receive electrical energy from the electrical energy storage device, the heating elements disposed near the exterior massaging surface of the elongated housing to transmit heat energy to the user.

16. The device of claim 15 wherein the heating elements are resistive heating elements.

17. The device of claim 1 further comprising an indicator light adapted to illuminate when the elongated housing has been moved generally along the axis in a reciprocating manner to store enough electrical energy in the electrical energy storage device to operate the device for its intended use.

18. The device of claim 17 wherein the indicator light illuminates when enough energy has been stored to operate the device for a predetermined period of time.

19. The device of claim 18 wherein the predetermined period of time is between 15 minutes and 5 hours.

20. The device of claim 1, wherein the exterior massaging surface includes at least one of a roller, a ball bearing, or a ribbed, flexible surface.

21. The device of claim 1, wherein the exterior massaging surface comprises a textured surface to provide a sexually pleasing contact surface.

22. A method comprising:
imparting a reciprocating motion to portable sexual stimulation device comprising:
an elongated housing that includes an exterior massaging surface configured to provide a sexually stimulating sensation, the elongated housing defining a longitudinal axis;
an electrical energy generating source operatively coupled to the elongated housing, the electrical energy generating source comprising a magnet and a charging coil, the magnet and charging coil adapted to move relative to one another during a reciprocating motion of the elongated housing generally along the longitudinal axis, the relative movement of the magnet and charging coil adapted to generate electrical energy in the coil;
a charging circuit adapted to receive electrical energy generated by the electrical energy generating source, the charging circuit comprising a rectifier and an electrical energy storage device;
a vibration motor coupled to the elongated housing, the vibration motor adapted to receive electrical energy from the electrical energy storage device, the vibration motor further adapted to impart vibrational energy to the elongated housing;
a switch adapted to deliver electrical energy from the electrical energy storage device to the vibration motor when the switch is closed;
delivering vibrational energy to a user so as to provide a sexually stimulating sensation.

* * * * *